United States Patent [19]

Helliwell

[11] Patent Number: 5,500,152
[45] Date of Patent: Mar. 19, 1996

[54] DETERGENT COMPOSITION

[75] Inventor: John F. Helliwell, Merseyside, United Kingdom

[73] Assignee: Lever Brothers Company, Division of Conopco, Inc., New York, N.Y.

[21] Appl. No.: 421,129

[22] Filed: Apr. 13, 1995

Related U.S. Application Data

[63] Continuation of Ser. No. 103,467, Aug. 6, 1993, abandoned.

[30] Foreign Application Priority Data

Aug. 7, 1992 [GB] United Kingdom ............... 9216854

[51] Int. Cl.$^6$ ................ C11D 1/219; C11D 1/90; C11D 1/28
[52] U.S. Cl. ............. 252/547; 252/546; 252/174.15; 252/174.23; 252/DIG. 15; 252/550
[58] Field of Search ............... 252/546, 547, 252/174.15, 174.23, DIG. 13, 550

[56] References Cited

U.S. PATENT DOCUMENTS

| | | | |
|---|---|---|---|
| 4,273,760 | 6/1981 | Koehler et al. | 424/70 |
| 4,321,156 | 3/1982 | Bushman | 252/142 |
| 4,812,253 | 3/1989 | Small et al. | 252/132 |
| 4,957,747 | 9/1990 | Stiefel | 424/691 |
| 5,085,857 | 2/1992 | Reid et al. | 424/70 |
| 5,132,037 | 7/1992 | Greene et al. | 252/108 |
| 5,152,914 | 10/1992 | Foster et al. | 252/174 |
| 5,180,584 | 1/1993 | Sebag et al. | 424/401 |
| 5,182,105 | 1/1993 | Takata et al. | 424/78.02 |
| 5,234,619 | 8/1993 | Greene et al. | 252/108 |
| 5,254,334 | 10/1993 | Ramirez et al. | 424/70 |
| 5,256,407 | 10/1993 | Gough | 424/71 |
| 5,275,755 | 1/1994 | Sebag et al. | 252/174.15 |
| 5,275,808 | 1/1994 | Murray et al. | 424/70 |
| 5,290,471 | 3/1994 | Green et al. | 252/108 |
| 5,302,322 | 4/1994 | Birtwistle | 252/547 |
| 5,308,551 | 5/1994 | Beauquey et al. | 252/548 |
| 5,422,280 | 6/1995 | Aelliwell et al. | 436/72 |

FOREIGN PATENT DOCUMENTS

| | | |
|---|---|---|
| 0203750 | 12/1985 | European Pat. Off. . |
| 432951 | 6/1991 | European Pat. Off. . |
| 457688 | 11/1991 | European Pat. Off. . |
| 3081400 | 4/1991 | Japan . |
| 2114995 | 9/1983 | United Kingdom . |
| 2170216 | 7/1986 | United Kingdom . |
| 2245585 | 1/1992 | United Kingdom . |

*Primary Examiner*—Paul Lieberman
*Assistant Examiner*—Michael P. Tierney
*Attorney, Agent, or Firm*—Ronald A. Koatz

[57] ABSTRACT

Shower gel compositions in the form of a liquid or gel comprising 5–50% wt. of a detergent comprising 30–100% wt. (on total detergent) of a fatty acyl isethionate and 0–70% wt (on total detergent) of other detergent, 0.01–5% on product of cationic polymer and 0.5–15% wt. by weight of silicone. The compositions show enhanced silicone deposition as compared with composition employing other surfactants.

8 Claims, No Drawings

DETERGENT COMPOSITION

This is a Continuation application of U.S. Ser. No. 08/103,467, filed Aug. 6, 1993 now abandoned.

This inventions relates to detergent compositions in liquid or gel form suitable for personal washing of either skin or hair.

It is known to include silicone in such compositions, either for hair conditioning or to enhance the feel of skin after washing. It is also known to include a cationic polymer along with the silicone.

Japanese published application 3-81400 (Toyo Beauty KK) discloses washing compositions based on soap which also contain silicone oil and cationic polymer.

EP-A-432951 describes shampoo formulations comprising sodium lauryl ether sulphate and betaine surfactants, Jaguar (RTM) cationic polymer and a silicone conditioner. EP-A-457688 (L'Oreal) discloses a shower gel which contains silicone oil an cationic polymer.

We have now found that cationic polymer enhances the deposition of silicone from such compositions to a varying extent which depends on the detergent which is included in the composition. This invention concerns the synergistic interaction of silicones with selected surfactants.

Deposition of silicone is enhanced by cationic polymer if the detergent in the compositions contains a substantial proportion of fatty acyl isethionate.

Thus, according to the present invention there is provided a detergent composition in the form of an aqueous liquid or gel containing 5% to 50% by weight of detergent which comprises:

(a) 30 to 100% by weight, based on the total detergent, of a fatty acyl isethionate of formula $$R-CO_2-CH_2CH_2-SO_3M$$

where R is an alkyl or alkenyl group of 7 to 21 carbon atoms and M is a solubilising cation such as sodium, potassium, ammonium or substituted ammonium;

(b) 0 to 70% by weight, based on the total detergent, of other detergent, ii) 0.01 to 5% by weight of cationic polymer iii) 0.5 to 15% by weight of silicone.

Particularly preferred is a detergent mixture in which the acyl isethionate is accompanied by zwitterionic detergent.

Acyl isethionates and the combination of acyl isethionates with zwitterionic detergents, such as betaines, are known components of many personal washing compositions. In the compositions of the present invention the surfactant systems are said to be mild in that they do not damage the stratum corneum, i.e. the outer layer of the skin. While not wishing to restrict the scope of the invention by reference to a theory of operation, it is believed that one would expect better deposition in the presence of a harsh surfactant such as soap, as the superficial skin damage resulting from the presence of this surfactant would lead to an increase in the surface area on which the silicone can deposit. In the absence of cationic polymer, experiment has shown that this is indeed the case. However we have determined that the combination of mild surfactant systems comprising isethionate, a silicone and a cationic polymer shows improved deposition as compared with equivalent systems in which the surfactant is harsh. Such systems therefore show both the mildness benefit due to the selection of surfactant and an enhanced deposition benefit due to this selection.

The various materials used in the invention, and preferred features, will now be described in turn.

Fatty acyl isethionate may be prepared by the reaction between alkali metal isethionate and aliphatic fatty acids (or their acid chlorides) having from 8 to 22 carbon atoms. Preferably these fatty acids have an iodine value of less than 20. Generally a mixture of aliphatic fatty acids will be used. In some forms of the invention at least three quarters of the fatty acyl groups in the acyl isethionate have from 12 to 18 carbon atoms while the balance, up to a quarter of the fatty acyl groups, may have from 8 to 10 carbon atoms. Notably the fatty acyl groups may be provided by coconut fatty acid.

Fatty acyl isethionate contributes to mildness towards skin and also contributes to obtaining foam of good volume and/or quality. Even fairly low levels of acyl isethionate will contribute to these benefits.

The amount of fatty acyl isethionate must be at least 30% by weight of the detergent in the composition. It may well be at least 35% or 40% and indeed may be at least 50% of the detergent present in the composition.

The fatty acyl isethionate may be the sole detergent present. However, its water solubility is rather low when used alone and preferably further detergent is present.

It is preferred that the detergent mixture comprises from 20 to 50% by weight of a zwitterionic detergent in which a hydrophilic head group contains both a quaternary nitrogen atom and at least one acid group which may be a carboxylic or a sulphonic acid group. Such detergents should generally include an alkyl or alkenyl group of 7 to 18 carbon atoms. They will usually comply with an overall structural formula $$R^1+\overset{O}{\overset{\|}{C}}-NH(CH_2)_m\xrightarrow{}_n\overset{R^2}{\underset{R^3}{\overset{|}{N^+}}}-X-Y$$

where $R^1$ is alkyl or alkenyl of 7 to 18 carbon atoms $R^2$ and $R^3$ are each independently alkyl, hydroxyalkyl or carboxyalkyl of 1 to 3 carbon atoms m is 2 to 4 n is 0 or 1

X is alkylene of 1 to 3 carbon atoms optionally substituted with hydroxyl, and

Y is $-CO_2^-$ or $-SO_3^-$

Suitable zwitterionic detergents within the above general formula include simple betaines of formula:

$$R^1-\overset{R^2}{\underset{R^3}{\overset{|}{N^+}}}-CH_2CO_2^-$$

and amido betaines of formula:

$$R^1-CONH(CH_2)_m-\overset{R^2}{\underset{R^3}{\overset{|}{N^+}}}-CH_2CO_2^-$$

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the zwitterionic detergent is a sulphobetaine of formula:

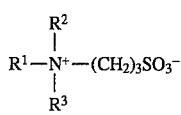

or

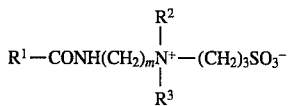

where m is 2 or 3, or variants of these in which —$(CH_2)_3SO_3^-$ is replaced by

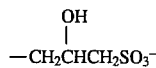

$R^1$, $R^2$ and $R^3$ in these formulae are as defined previously.

Other anionic detergents beside acyl isethionate may be present notably in quantities from 10 to 50% of the detergent mixture. Anionic detergent which is particularly envisaged is alkyl ether sulphate of the formula:

where $R^4$ is alkyl or alkenyl of 8 to 18 carbon atoms, especially 11 to 15 carbon atoms, t has an average value of at least 2.0 and M is a solubilising cation such as sodium, potassium, ammonium or substituted ammonium. Preferably t has an average value of 3.

Other possible anionic detergents include alkyl glyceryl ether sulphate, sulphosuccinates, taurates, sarcosinates, sulphoacetates, alkyl phosphates and acyl lactates. Sulphosuccinates may be monoalkyl sulphosuccinates having the formula:
$R^5O_2CCH_2CH(SO_3M)CO_2M$; and amido-MEA sulphosuccinates of the formula: $R^5CONHCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein R ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

The anionic detergent included in the composition will generally be selected to avoid harsh detergent such as primary alkane sulphonate or alkyl benzene sulphonate. The amount, if any, of these is preferably less than 3% of the detergents present.

Alkanolamide detergents are preferably included at only a low level, if at all, since they have been found to reduce mildness. Preferably they are restricted to not more than 5% by weight of the detergent mixture. Even better is to exclude alkanolamides and the harsh anionics, alkyl benzene sulphonate and primary alkane sulphonate completely. It is also preferred that amine oxide is not more than 5% by weight of the detergent mixture, since this has been found to reduce lather quality.

The total quantity of detergent in the composition will generally not exceed 25% by weight. The amount may well not exceed 20%. The amount will often be at least 8% or even at least 10% by weight.

The amount of cationic polymer is preferably at least 0.05% by weight of the whole composition. It may well not exceed 3% or even 2% of the composition.

Various cationic polymers may be used. Examples of cationic polymers include the cationic cellulose ethers described in U.S. Pat. Nos. 3,816,616 and 4,272,515 and which are available commercially from Union Carbide Corp. under the trade mark POLYMER JR. Other suitable materials are the cationic polygalactomannan gum derivatives described in U.S. Pat. No. 4,298,494 which are commercially available under the trade mark JAGUAR from Celanese-Stein Hall. An example of a suitable material is the hydroxypropyltrimethylammonium derivative of guar gum of the formula:

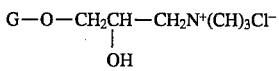

where G represents guar gum. Such a material is available under the name JAGUAR C-13-S. This material also has the CTFA designation Guar Hydroxypropyltrimonium Chloride. In JAGUAR C-13-S the degree of substitution of the cationic groups is about 0.13. Another possible material is that known as JAGUAR C-17 which is similar to JAGUAR C-13-S but has a higher degree of substitution of cationic groups of about 0.25–0.31. A further example of a guar derivative is the hydroxypropylated cationic guar derivative known as JAGUAR C-16 which as well as containing the above cationic quaternary ammonium groups also contain hydroxypropyl (—$CH_2CH(OH)CH_3$) substituent groups. In JAGUAR C-16 the degree of substitution of the cationic groups is 0.11–0.16 and the moles of substitution of hydroxypropyl groups is 0.8–1.1.

Other cationic polymers include cationic polyamide polymers such as the low molecular weight adipic acid/diethylene-triamine polyamide and the copolymers of vinylpyrrolidone and dimethylaminoethyl methacryate quaternised with dimethyl sulphate (Gafquat 755, GAF Corporation) described in U.S. Pat. No. 4,080,310; the graft cationic copolymer containing N-vinylpyrrolidone, dimethylaminoethyl methacrylate and polyethylene glycol described in U.S. Pat. No. 4,048,301; the mineral acid salts of the amino-alkyl esters of homo- and copolymers of unsaturated carboxylic acids having from 3 to 5 carbon atoms described in U.S. Pat. No. 4,009,256; and the polymers of etherified starch described in U.S. Pat. No. 3,186,911.

THe high molecular weight cationic polymers are sold under the trade mark MERQUAT by Merck & Co., Inc. Representative ones are Merquat 100, a highly charged cationic dimethyldiallylammonium chloride homopolymer, and Merquat 550, a highly charged cationic copolymer prepared with dimethyldiallylammonium chloride and acrylamide. These materials are designated in the CTFA dictionary as Quaternium-40 and Quaternium-41, respectively.

It is preferred that the amount of silicone is at least 2% by weight of the composition and preferably at least 3% or 3.5%. The amount will generally not exceed 10% or even 8%.

Silicone may be an involatile silicone oil or a relatively more volatile silicone. An involatile silicone oil will generally have a viscosity of at least 5 centistokes at 25° C., e.g. 10 to 100,000 centistokes. In fact, involatile silicones are highly preferred for the invention.

Suitable silicones include polyalkyl or polyaryl siloxanes with the following structure:

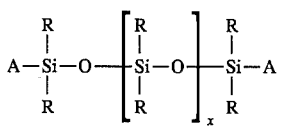

wherein R is alkyl or aryl, x is an integer from about 100 to about 2,400 and A represents groups which block the ends of the silicone chains. Suitable A groups include methyl, methoxy, ethoxy, propoxy, and aryloxy. The two R groups on each silicone atom may represent the same group or different groups. Preferably the two R groups represent the same group. Suitable R groups include methyl, ethyl, propyl, phenyl, methylphenyl and phenylmethyl. The preferred silicones are polydimethyl siloxane, polydiethylsiloxane, and polydimethylphenylsiloxane. Polydimethylsiloxane is especially preferred.

Other silicones suitable for use in the present invention include the cyclic silicones. These materials have the formula:

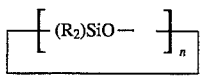

where n is 4 or 5 and R has the same meaning as in the structure of linear siloxanes.

The dimethyl cyclic siloxanes are volatile, and are thus present only temporarily after deposition. Volatile cyclic silicones are available under the trade name DOW CORNING 344 and 345 fluids from the Dow Corning Corporation.

Silicone used in this invention may well be a silicone homopolymer, although silicones may be modified by including copolymers, e.g. polyethers as is described in U.S. Pat. No. 3,957,970. Such copolymers tend to be more soluble than homopolymers of silicone.

Other materials may be included in compositions of this invention. Possibilities include colouring agents, opacifying agents, organic polymers, perfumes including deodorant perfumes, bactericidal agents to reduce the microflora on skin, antioxidants and other preservatives.

Organic polymers which may be present include cross-linked polyacrylates such as the Carbopol (TM) polymers available from Goodrich. These can function to increase viscosity or enhance stability of a composition. Polysaccharides are also well known as thickening agents and many are cellulose or cellulose derivatives.

The compositions of this invention will generally be pourable liquids or semi-liquids, although they may be somewhat viscous. For this, they may be thickened by including electrolyte, and/or perfume.

Compositions of this invention may be formulated as products for washing the skin, e.g. bath or shower gels, hand washing compositions or facial washing liquids. They may also be formulated as hair shampoos.

A viscosity of at least 500 centipoise (0.5 Pa.sec) at a low shear rate of 10 to 25 $sec^{-1}$ may be desired for most product forms. Hair shampoos will generally have a viscosity of at least 1000 centipoise at such shear rate. Products for washing the skin are customarily more viscous. A viscosity of at least 5000 centipoise or better at least 7000 centipoise at the same shear rate is usually appropriate for these.

Compositions according to this invention are emulsions with the silicone present as a disperse phase. Such emulsions can be formed by mixing the ingredients under conditions of high shear. However it may be preferred to utilise a preformed emulsion so as to simplify mixing the composition.

It is preferred that the dispersed droplets of silicone oil have a particle size not greater than 2 μm preferably 0.1–1 μm, to enhance stability.

It has been found that a composition of this invention has especially good stability when formulated (e.g. thickened with electrolyte) to have a viscosity of at least 6000 centipoise at 10 $sec^{-1}$ shear rate at 25° C. Such a viscosity is appropriate for a composition for washing the skin, such as a shower gel.

For compositions of viscosity below 5000 centipoise at 10 $sec^{-1}$ shear rate, such as hair shampoos, it will generally be desirable to include a substance which structures the emulsion and thereby enhances stability.

Examples of such substances known in the art are distearates of dihydric alcohols such as ethyleneglycol and oligomers thereof.

Other materials which have been proposed for inclusion to enhance stability of silicone emulsions include alcohols with two alkyl chains giving a total of more than 20 carbon atoms.

Thus a preferred form of the invention is a composition for washing the skin, having a viscosity of at least 6000 centipoise at 10 $sec^{-1}$ shear rate and containing dispersed silicone oil in droplets with a particle size not exceeding 2μm.

Such a composition can provide a valuable combination of good mildness, silicone deposition on the skin and very good storage stability without requiring such structuring compounds as esters and alcohols having two alkyl or acyl groups with more than 20 carbon atoms in total, various acyl derivatives in which the acyl groups each contain at least 16 carbon atoms Scleroglucan gums and amine oxides incorporating alkyl groups with at least 16 carbon atoms. Such compounds are then preferably absent or if present, are included in an amount less than 0.5%.

A particularly preferred embodiment of the invention comprises an aqueous liquid or gel containing a) 10–20% wt of surfactant, said surfactant comprising at least 50% on total surfactant of a fatty acyl isethionate of formula:

$$R—CO_2—CH_2CH_2—SO_3M$$

where R is an alkyl of 8–14 carbon atoms and M is a solubilizing cation selected from the group comprising sodium potassium and ammonium, said surfactant further comprising at least 10% on total surfactant of a betaine, b) 0.01–5% wt. of a cationic polymer, and, c) 0.5–15% wt. of a non-volatile silicone oil having a viscosity of at least 5 centistokes at 25° C., said silicone oil being present as droplets having a mean possible size of 0.1–1 μm.

EXAMPLES

In the Examples which follow a number of tests were carried out by human volunteers. The experimental procedure employed was as follows:

The volunteer washed one forearm with a control shower gel containing neither silicone nor cationic polymer. This was carried out by wetting the arm and also the volunteer's free hand with warm water then using the free hand to lather the arm with 0.5 grams of the control shower gel, next rinsing for 10 seconds while rubbing with the free hand and then drying the arm with a paper towel.

After this pre-washing the volunteer washes the same forearm with a test product using the same procedure. When drying the forearm care is taken that the paper towel is drawn only once across a test area of the forearm.

10 minutes after drying the forearm the volunteer presses a strip of adhesive tape onto the area keeping it in place for 30 seconds using a spring loaded device bearing on a rubber bung to press the tape onto the skin with a repeatable pressure of 85g.cm$^{-2}$. The adhesive tape employed was J-Lar superclear (TM) tape having a width of 25 mm.

5 or more such strips of tape are applied in this way one after another, to the same area of skin.

In this test procedure silicone which has deposited on the skin will subsequently be transferred to the tape along with some of the outer layer of the volunteer's skin.

The amounts of silicone and skin adhering to the tape are determined by means of X-ray fluorescence spectroscopy. The tape strips are placed in an X-ray fluorescence spectrometer with the adhesive side facing the beam of this machine. A mask is applied over the tape to expose only a standardised area in the middle of the tape to the X-ray beam. The sample chamber of the machine is placed under vacuum before making measurements and the spectrometer is then used to measure the quantities of silicon and sulphur. The sulphur is representative of the amount of skin which has transferred to the tape.

The amounts of silicon and sulphur observed with a clean piece of adhesive tape are subtracted from the experimental measurements. The experimental measurements for successive pieces of tape are added together and the cumulative totals of silicon and sulphur are expressed as a ratio of silicon to sulphur.

Example 1

A shower gel contained the following:

|  | % by weight |
|---|---|
| Sodium cocoyl isethionate | 9.0 |
| Coconut betaine | 6.0 |
| Silicone oil | 5.0 |
| Jaguar C-13-S | 0.1 |
| Formalin | 0.1 |
| Water | balance to 100% |

The sodium cocoyl isethionate was Fenopon (Registered Trade Mark) AC78 available from GAF Corporation. The coconut betaine was of formula:

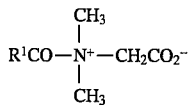

in which R$^1$CO— is a mixture of acyl groups derived from coconut. This betaine was Empigen (Registered Trade Mark) BB from Albright and Wilson.

As mentioned previously, Jaguar C-13-S is a cationic guar gum derivative with the CTFA designation guar hydroxypropyltrimonium chloride, available from Celanese-Stein Hall.

The silicone was added as 10% of a preformed emulsion BY22–026 from Toray Silicone Co Ltd comprising:

| Lauryl alcohol ethoxylate 2EO | 2% |
|---|---|
| Lauryl alcohol ethoxylate 21EO | 2% |
| Polydimethyl siloxane (60,000 cS) | 50% |
| Preservative | qs |
| Water | balance to 100% |

The silicone particles in this emulsion have a mean particle size of 0.4 μm.

The shower gel composition was made by mixing all the ingredients in a paddle stirrer. This led to a composition with a viscosity measured as 15,000 centipoise at 10 sec$^{-1}$.

Silicone deposition by this composition was measured by the test procedure described above. It was compared with silicone deposition from an identical composition omitting the Jaguar C-13-S.

The cumulative results from 8 test strips were:

|  | Total Si | Total S | Si/S Ratio |
|---|---|---|---|
| with Jaguar | 2.8 | 4.7 | 0.60 |
| without Jaguar | 0.4 | 4.4 | 0.09 |

Example 2

A shower gel contained the following:

|  | % by weight |
|---|---|
| Sodium cocoyl isethionate | 5.0 |
| Coconut amidopropyl betaine | 8.0 |
| Sodium lauryl ether sulphate 3EO | 2.0 |
| Silicone oil | 5.0 |
| Jaguar C-13-S | 0.1 |
| Formalin | 0.1 |
| Perfume | 1.0 |
| Water | balance to 100% |

The coconut isethionate was Fenopon AC78 as in the previous Example.

The coconut amidopropyl betaine was of the formula:

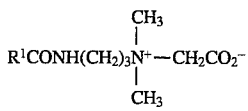

in which R$^1$CO— is a mixture of acyl groups derived from coconut. This was Rewoteric AMB 14 (TM) from Rewo.

The sodium lauryl ether sulphate was Empicol 0251 (TM) from Albright and Wilson.

The silicone was BY22-026 emulsion as in the previous Example.

Again the shower gel was made by mixing the ingredients. Viscosity of the composition was measured as 15,000 centipoise at 10 sec$^{-1}$.

Silicone deposition was measured by the procedure described, and compared with that from an identical composition without the Jaguar C-13-S. The cumulative results from 8 test strips were:

|  | Total Si | Total S | Si/S Ratio |
|---|---|---|---|
| with Jaguar | 2.0 | 4.9 | 0.41 |
| without Jaguar | 0.6 | 5.2 | 0.12 |

Comparative Example

A liquid soap composition contained:

|  | % by weight |
| --- | --- |
| Soap | 15.0 |
| Silicone oil | 5.0 |
| Jaguar C-13-S | 0.1 |
| Formalin | 0.1 |
| Water | balance to 100% |

The soap was a mixture of the sodium salts of oleic acid and coconut fatty acid. The silicone was BY22–026 from Toray Silicone. The composition was prepared using a paddle stirrer as before, and was very viscous.

Silicone deposition was determined and compared with deposition from a similar composition without Jaguar. The cumulative results from 8 test strips were:

|  | Total Si | Total S | Si/S Ratio |
| --- | --- | --- | --- |
| with Jaguar | 1.2 | 3.8 | 0.32 |
| without Jaguar | 1.1 | 4.5 | 0.24 |

It is clear from these figures that with soap as the detergent in a composition the deposition of silicone is low and not much enhanced by including Jaguar C-13-S, whereas in Examples 1 and 2 the presence of Jaguar C-13-S causes a very substantial increase in silicone deposition.

I claim:

1. A detergent composition in the form of an aqueous liquid or gel comprising:

(1) about 5% by weight total composition of a fatty acyl isethionate or mixtures of fatty acyl isethionates having the formula:

$$RCO_2CH_2CH_2SO_3M$$

wherein R is an alkyl or alkenyl group of 7 to 21 carbon atoms and M is a solubilizing cation selected from the group consisting of sodium, potassium, ammonium and substituted ammonium;

(2) about 8% by weight total composition of a zwitterionic surfactant having the formula:

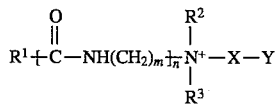

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

m is 2 to 4 n is 0 or 1

X is alkylene of 1 to 3 carbon atoms optionally substituted with hydroxyl;

and

Y is $-CO_2^-$ or $-SO_3^-$;

(3) about 2.0% by wt. of total composition alkoxylated or non-alkoxylated alkyl ether sulphate;

(4) 0.5 to 15% by wt. of composition silicone;

(5) 0.01 to 5% by wt. of composition of a cationic polymer selected from the group consisting of cationic cellulose ethers and cationic polygalactomannan gums; and (6) balance water, electrolyte and 2. A composition according to claim 1 wherein the isethionate is a mixture of isethionate having varying chain lengths and at least three quarters of the groups R of the mixture of acyl isethionates are alkyl of 11 to 17 carbons.

3. A composition according to claim 1 comprising 0.05% to 2.0% by weight cationic.

4. A composition according to claim 1 wherein the silicone is a polysiloxane with the structure

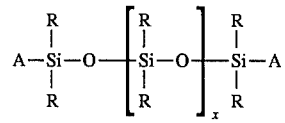

wherein R is alkyl or aryl, x is an integer from about 100 to about 2,400 and A represents groups which block the ends of the silicone chains.

5. A composition according to claim 1 containing 2% to 8% by weight of silicone.

6. A composition according to claim 1 wherein the silicone oil has a viscosity of at least 5 centistokes at 25° C.

7. A composition according to claim 1 wherein the electrolyte is an inorganic electrolyte.

8. A composition according to claim 1 which includes inorganic electrolyte and has a viscosity of at least 6,000 centipoise at a shear rate of 10 sec$^{-1}$.

\* \* \* \* \*